(12) United States Patent  
Kilbey

(10) Patent No.: US 9,107,738 B2  
(45) Date of Patent: Aug. 18, 2015

(54) LUMBAR BELT WITH POCKETS WHICH FACILITATE INSTALLATION

(71) Applicant: Bryan E. Kilbey, DeFuniak Sprs, FL (US)

(72) Inventor: Bryan E. Kilbey, DeFuniak Sprs, FL (US)

(*) Notice: Subject to any disclaimer, the term of this patent is extended or adjusted under 35 U.S.C. 154(b) by 259 days.

(21) Appl. No.: 13/863,445

(22) Filed: Apr. 16, 2013

(65) Prior Publication Data

US 2014/0309571 A1     Oct. 16, 2014

(51) Int. Cl.
*A61F 5/00* (2006.01)
*A61F 5/02* (2006.01)
*A61F 7/10* (2006.01)
*A61F 7/02* (2006.01)

(52) U.S. Cl.
CPC . *A61F 5/028* (2013.01); *A61F 7/10* (2013.01); *A61F 2007/0228* (2013.01); *A61F 2007/0231* (2013.01)

(58) Field of Classification Search
CPC ... A45F 5/021; A45F 2200/0516; A45F 5/00; A45F 3/14; A45F 5/02; A45F 2003/144; A45F 3/04; A45F 3/047; A45F 2003/003; A45F 2003/006; A45F 2003/007; A45F 2003/146; A45F 2003/148

USPC .......................................... 602/19; 2/336–338
See application file for complete search history.

(56) References Cited

U.S. PATENT DOCUMENTS

| | | | | |
|---|---|---|---|---|
| 3,227,337 A * | 1/1966 | Santo, Jr | ........................ | 224/251 |
| 3,919,615 A * | 11/1975 | Niecke | ........................ | 320/112 |
| 5,381,801 A * | 1/1995 | McShane et al. | ............. | 128/848 |
| 7,007,832 B1 * | 3/2006 | Payne | ........................ | 224/660 |
| 2006/0289585 A1 * | 12/2006 | Godshaw et al. | ............. | 224/625 |

* cited by examiner

*Primary Examiner* — Michael Brown
(74) *Attorney, Agent, or Firm* — J. Wiley Horton

(57) ABSTRACT

The present invention provides methods to facilitate installation of a lumbar belt. The methods involve looping a belt around a person's abdomen. The belt provides a pocket on each end of the belt to allow the user easier application and tightening of the belt. In the preferred embodiment, each pocket is divided into two sections—thumb pocket and finger pocket. The user places one hand located within its corresponding pocket around the abdomen positioning the belt. The user then places the other hand located in its corresponding pocket over to meet the hand on the abdomen. The belt then is secured and remains in position around the abdomen. A cover panel also may be provided as a part of the belt to allow convenient access to a person's lumbar area.

20 Claims, 16 Drawing Sheets

LUMBAR BELT WITH POCKETS WHICH FACILITATE INSTALLATION

CROSS-REFERENCES TO RELATED APPLICATIONS

This application is a non-provisional application claiming priority to U.S. Provisional Application No. 61/624,695 filed on Apr. 16, 2012.

STATEMENT REGARDING FEDERALLY SPONSORED RESEARCH OR DEVELOPMENT

Not Applicable.

MICROFICHE APPENDIX

Not Applicable

BACKGROUND OF THE INVENTION

1. Field of the Invention

This invention relates to the field of medical products. More specifically, the invention comprises lumbar belt which allows for easier application and adjustment. The lumbar belt may be used in a variety of therapies, including cryotherapy.

2. Description of the Related Art

Lumbar belts are used as part of a variety of therapies. One example is the use of a "cold therapy" (also known as "cryo therapy") to minimize swelling following a surgical procedure. Cryo therapy assumes a variety of forms—ranging from simple ice or gel packs to sophisticated chilled water circulating devices.

One common application for cryo therapy is in post-surgical swelling reduction for lumbar spinal surgery. It is known to use a compressive "belt" to hold cold packs in position over the person's lumbar spine. The "belt" needs to be properly positioned and easily adjustable for the user. The present invention provides features and methods to facilitate the installation and provide for quick adjustments for such a belt.

BRIEF SUMMARY OF THE PRESENT INVENTION

The present invention comprises methods for applying a belt around a user's abdomen and adjusting the belt while it remains on the user. The belt has a pocket located on its right side and left side. One hand is place in its corresponding pocket and that portion of the belt is pressed against the user's abdomen. The belt is then wrapped around the abdomen. The other hand is placed in its corresponding pocket and is place over the hand currently located on the user's abdomen. The opposite ends of the belt then are connected and secured around the abdomen. In the preferred embodiment, the pockets are divided into two sections—thumb pocket and finger pocket. Additional methods are disclosed for the application of cold packs to a person's lumbar area. The cold packs may be attached directly to the belt or to a cover panel that may accompany the belt. The cover panel allows cold packs to be placed on the lumbar area without the removal of the belt. At least one side of the cover panel is detached from the belt exposing the person's lumbar area. One or more cold packs then may be attached to the inward facing surface of the cover panel. The cover panel is reattached to the belt.

Figure 1:
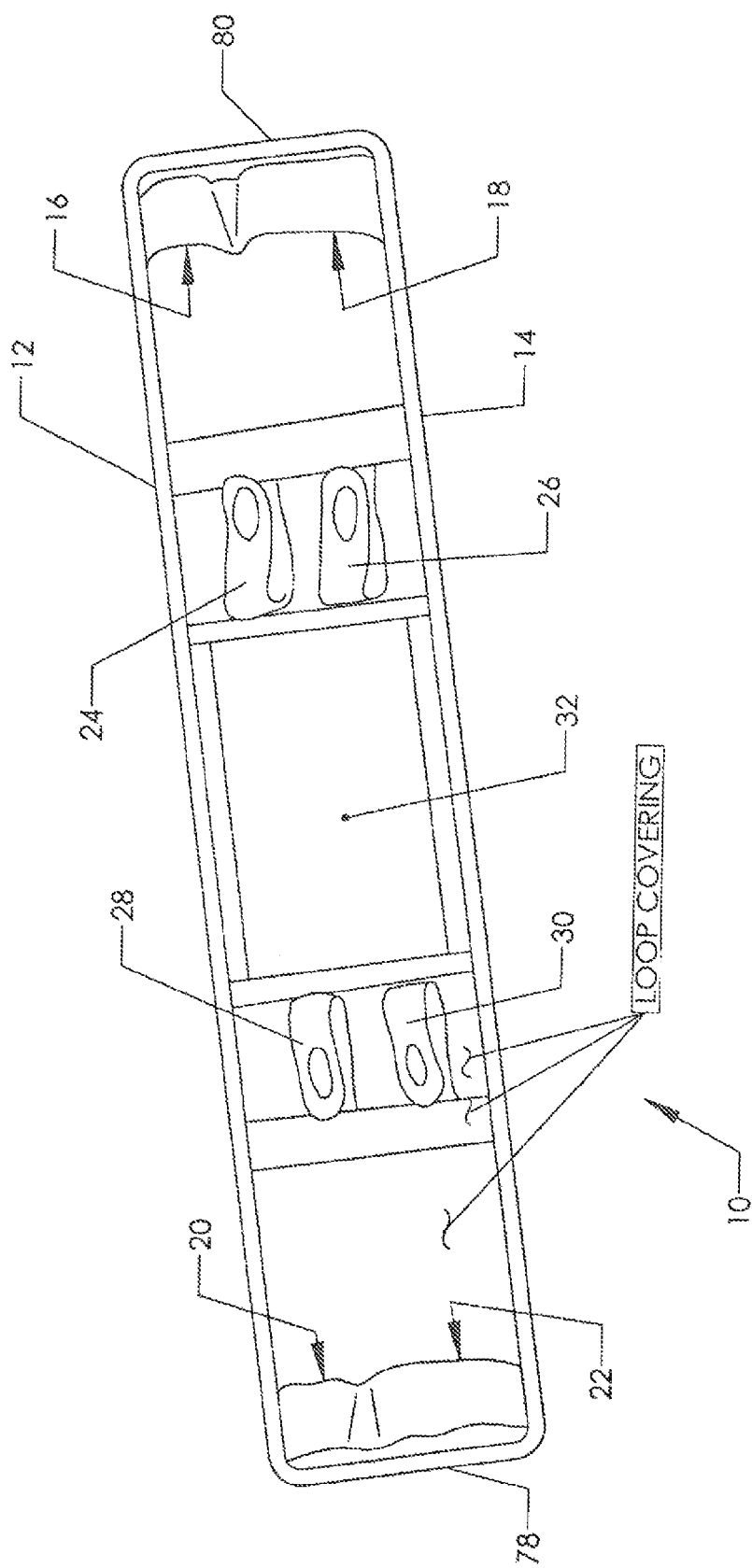
FIG. 1 is a perspective view, showing the belt portion of the present invention.

| REFERENCE NUMERALS IN THE DRAWINGS | | | |
|---|---|---|---|
| 10 | belt | 12 | top edge |
| 14 | bottom edge | 16 | right thumb pocket |
| 18 | right finger pocket | 20 | left thumb pocket |
| 22 | left finger pocket | 24 | tension strap |
| 26 | tension strap | 28 | tension strap |
| 30 | tension strap | 32 | window |
| 34 | loop panel | 36 | 4-way stretch panel |
| 38 | cover panel | 40 | main body |
| 42 | stay pocket cover | 44 | strap loop |
| 46 | strap loop | 48 | strap loop |
| 50 | strap loop | 54 | lumbar stay |
| 56 | stay pocket | 58 | hook tab |
| 60 | inward facing surface | 62 | left hook panel |
| 64 | right hook panel | 66 | assembly |
| 68 | hand | 70 | left hand |
| 72 | right hand | 73 | abdominal pad |
| 74 | hook panel | 76 | hook panel |
| 78 | left edge | 80 | right edge |
| 82 | soft surface | 112 | cold pack |
| 114 | vent | 116 | relief |
| 118 | hook panel | | |

DETAILED DESCRIPTION OF THE INVENTION

FIG. 1 shows the outward facing side of belt 10. The belt 10 is generally rectangular, being bounded by top edge 12, bottom edge 14, right edge 80 and left edge 78. A substantial portion of the outward facing side of belt 10 is covered in loop covering. The loop covering can be made of any material that is similarly found in a VELCRO® loop fastener.

In the embodiment shown in FIG. 1, a window 32 is provided in the middle of the belt 10. The window 32 provides convenient access to a person's lumbar area. Further, tension straps 24, 26 lie on the right side of window 32 and tension straps 28, 30 lie on the left side of window 32. Tension straps 24,26,28,30 are an example of the attachment features provided around the window 32 in order to attach a cover panel 38 (to be discussed later) to belt 10. Tension straps 24,26,28, 30 preferably include an elastic portion to allow flexibility. The free end of each tension straps 24,26,28,30 preferably includes hook panels (facing assay from the viewer in FIG. 1). The hook panels are made of any material that is similarly found in a VELCRO® hook fastener. The outward facing side of the anchored portion of each tension straps 24,26,28,30 preferably is covered in loop covering. The loop covering can be made of any material that is similarly found in a VEL-CRO® loop fastener. The free end of the tension straps 24,26, 28,30 may be pressed back against the anchored portion of the respective tension straps 24,26,28,30—or any other portion of the outward facing side of the belt 10 which is covered by loop covering.

Pockets are provided proximate to the right edge 80 and left edge 78 of belt 10. The right pocket has its opening accessible from the outward facing side of belt 10. The opening of the right pocket is facing away from the right edge 80 and the closed end is opposite the opening. Similarly, the left pocket has its opening accessible from the outward facing side of belt 10. The opening of the left pocket is facing away from the left edge 78 and the closed end is opposite the opening. The pocket may be completely closed or only partially closed. It could also be "closed" via segregating the thumb and finger pocket with a stitched web in between. The pockets assist the user in applying belt 10—as will be explained subsequently. In the embodiment shown in FIG. 1, each pocket is divided into a finger pocket and a thumb pocket. Thus, the right pocket proximate right edge 80 is divided into right thumb pocket 16 and right finger pocket 18. Similarly, the left pocket proximate to left edge 78 is divided into left thumb pocket 20 and left finger pocket 22. The outward facing sides of thumb pockets 16, 20 and finger pockets 18, 22 are optionally covered in loop covering. The loop covering can be made of any material that is similarly found in a VELCRO® loop fastener.

Figure 2:
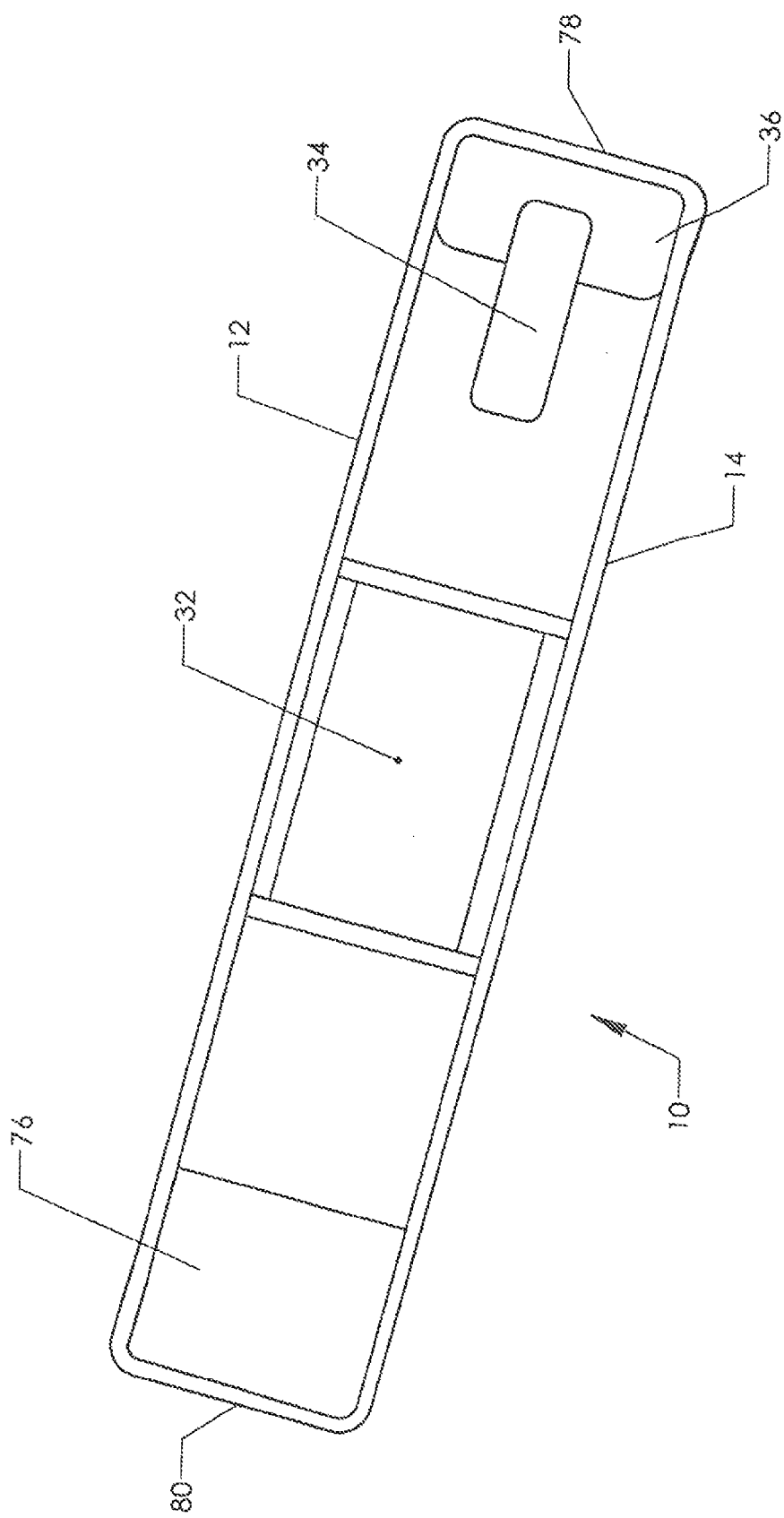
FIG. 2 is a perspective view, showing the opposite side of the belt of FIG. 1.

FIG. 2 shows the inward facing side of belt 10. The inward facing side provides a hook panel 76 proximate to right edge 80. The hook panel 76 is made of any material that is similarly found in a VELCRO® hook fastener. An elongated loop panel 34 is provided proximate left edge 78. The loop panel is covered in loop covering. The loop covering can be made of any material that is similarly found in a VELCRO® loop fastener. A 4-way stretch panel 36 is also provided proximate to the left edge 78.

Figure 3:
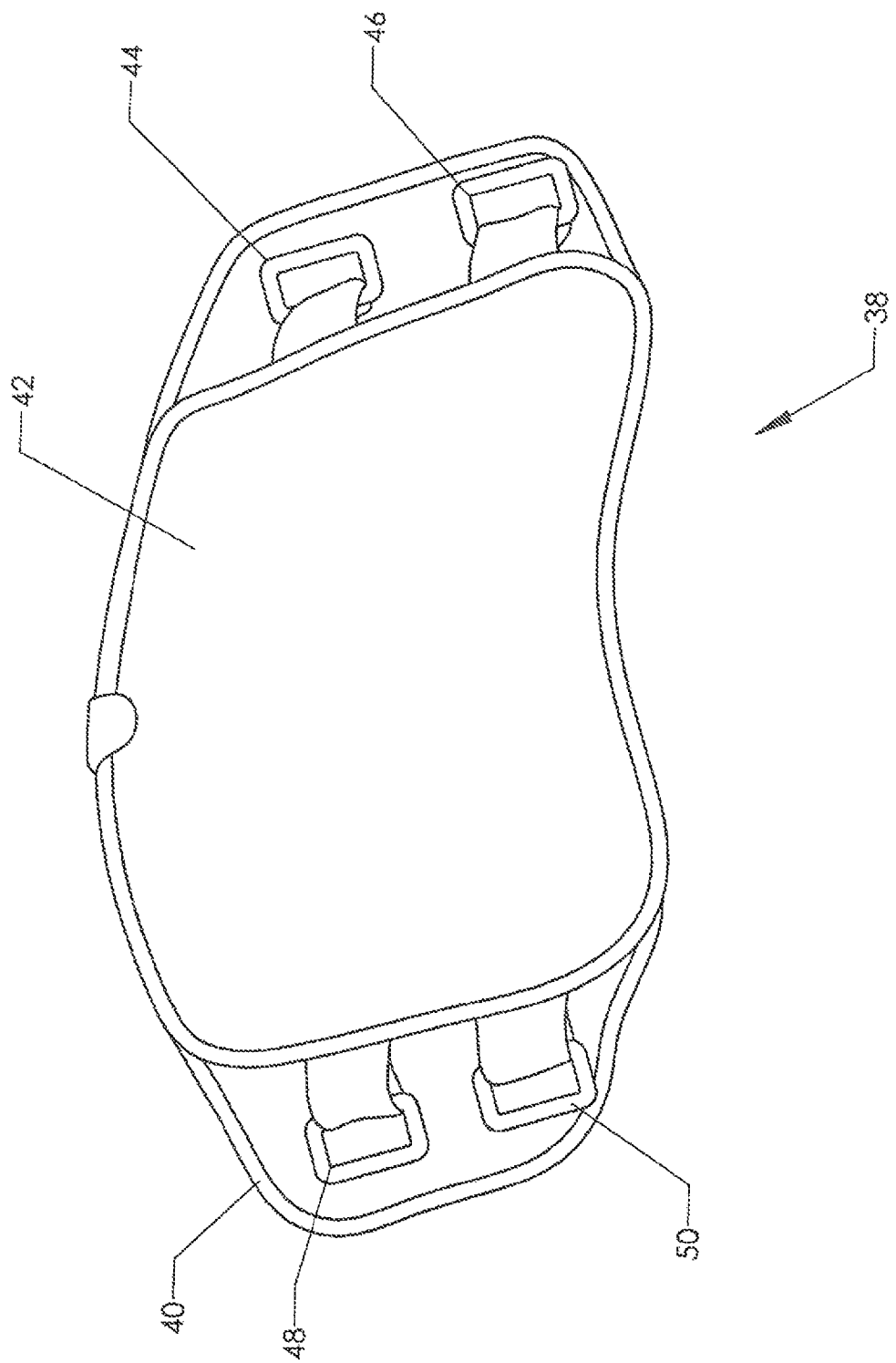
FIG. 3 is a perspective view, showing a cover panel which is used in conjunction with the belt.

FIG. 3 shows the outward facing surface of cover panel 38. The cover panel 38 has main body 40 and stay pocket cover 42. A substantial portion of the exterior of stay pocket cover 42 is covered in loop covering. The loop covering can be made of any material that is similarly found in a VELCRO® loop fastener.

Attachment features are provided to facilitate the attachment of the cover panel 38 to the belt 10. In the embodiment shown in FIG. 3, strap loops 44, 46 lie on the right side of the stay pocket cover 42 and strap loops 48, 50 lie on the left side of stay pocket cover 42. Strap loops 44,46,48,50 cooperate with the tension straps 24, 26, 28, 30 found on belt 10.

Figure 4:
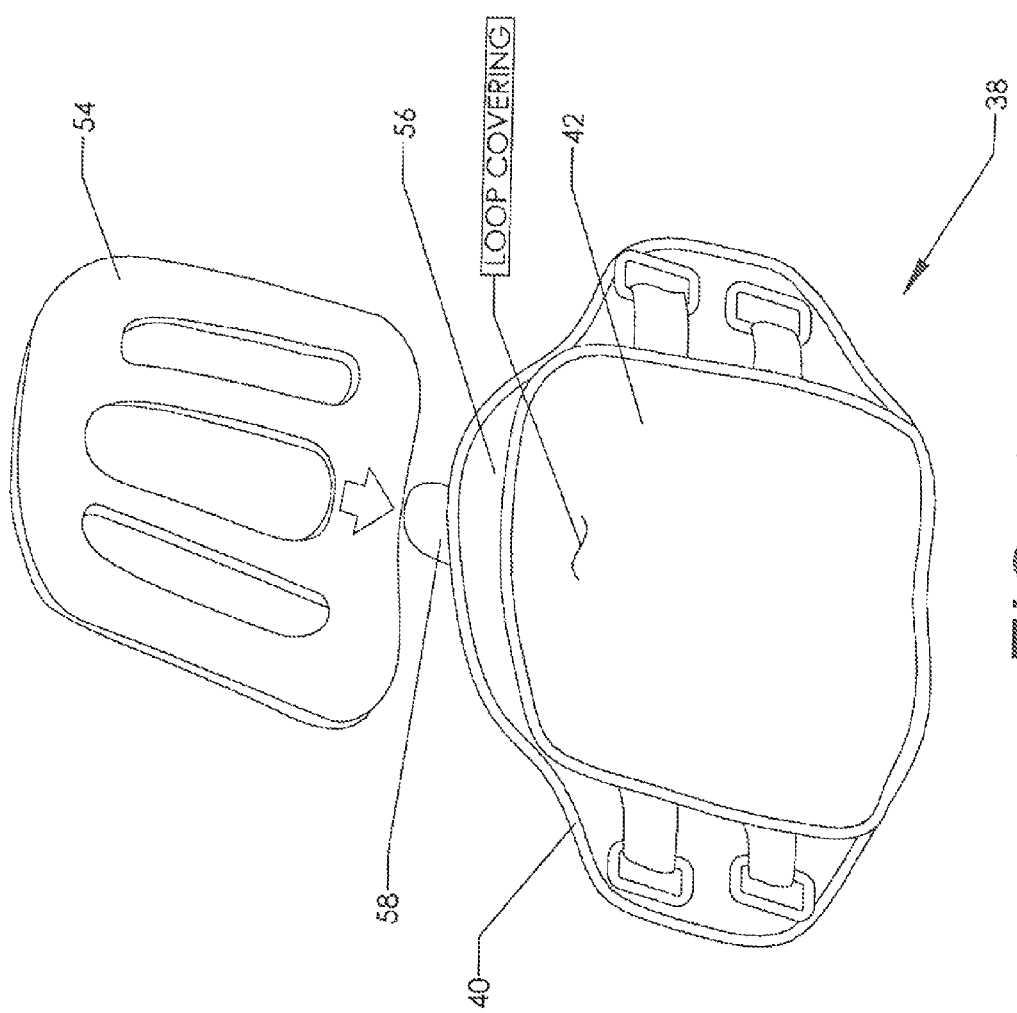
FIG. 4 is an exploded perspective view, showing the inclusion of a lumbar stay in the cover panel.

FIG. 4 is an exploded view of cover panel 38. In the embodiment as shown in FIG. 4, cover panel provides a stay pocket 56 with a hook tab 58. Stay pocket 56 is formed between main body 40 and stay pocket cover 42. Hook tab 58 preferably includes a hook panel. The hook panel is made of any material that is similarly found in a VELCRO® hook fastener. Hook tab 58 may be curled over the top and secured to the loop covering on the exterior of stay pocket cover 42.

Stay pocket 56 may optionally be used to house lumbar stay 54. As shown in FIG. 4, lumbar stay 54 is inserted into stay pocket 56 through the top opening. Lumbar stay 54 is preferably a semi-rigid material such as a sheet of flexible plastic. It is preferably contoured to match the shape of the user's lumbar area. It is possible to provide a variety of different shapes for lumbar stay 54. It is also possible to provide an embodiment in which lumbar stay 54 may be selectively deformed.

Figure 5:
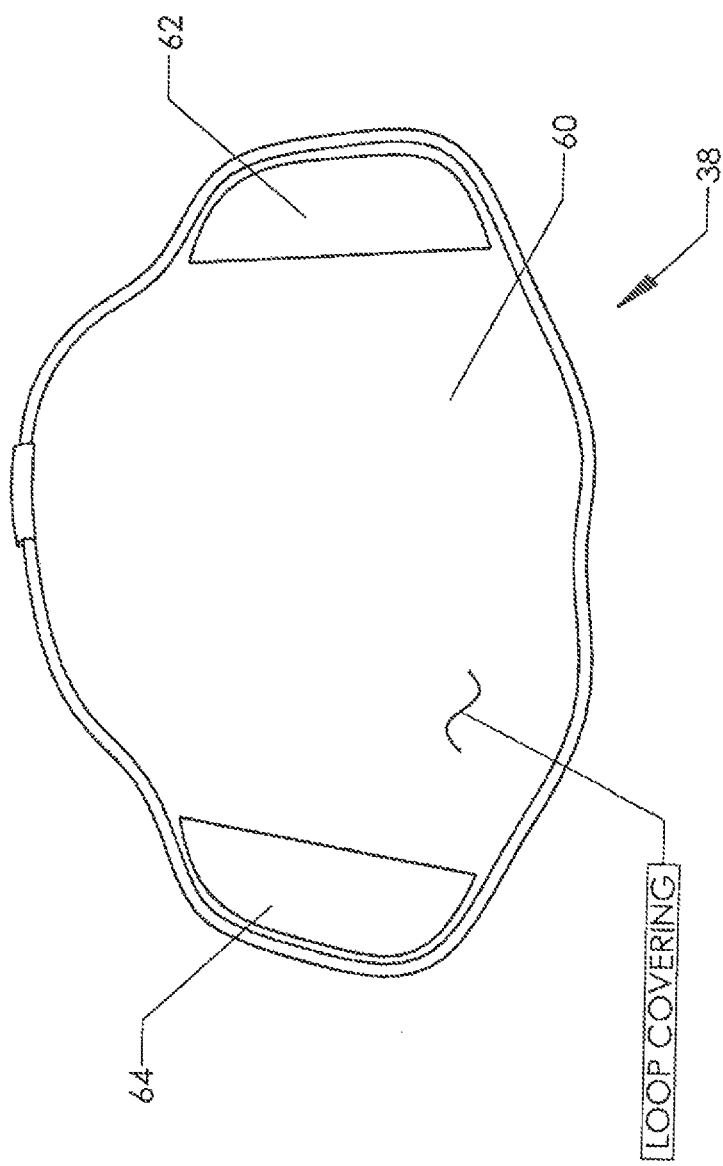
FIG. 5 is a perspective view, showing the lumbar panel from the opposite side.

FIG. 5 shows the inward facing surface of cover panel 38. Inward facing surface 60 is the surface which faces the user of the belt 10. A substantial portion of the inward facing surface 60 is covered in loop covering. The loop covering can be made of any material that is similarly found in a VELCRO® loop fastener. In the embodiment shown in FIG. 5, left hook panel 62 and right hook panel 64 provide an intermediate securing means for cover panel 38. Hook panels 62, 64 are made of any material that is similarly found in a VELCRO® hook fastener. Hook panels 62, 64 can be pressed against the loop covering on the outward facing side of belt 10 in order to hold cover panel 38 in position before the tension straps 24,26,28,30 are suitably tightened.

Figure 6:
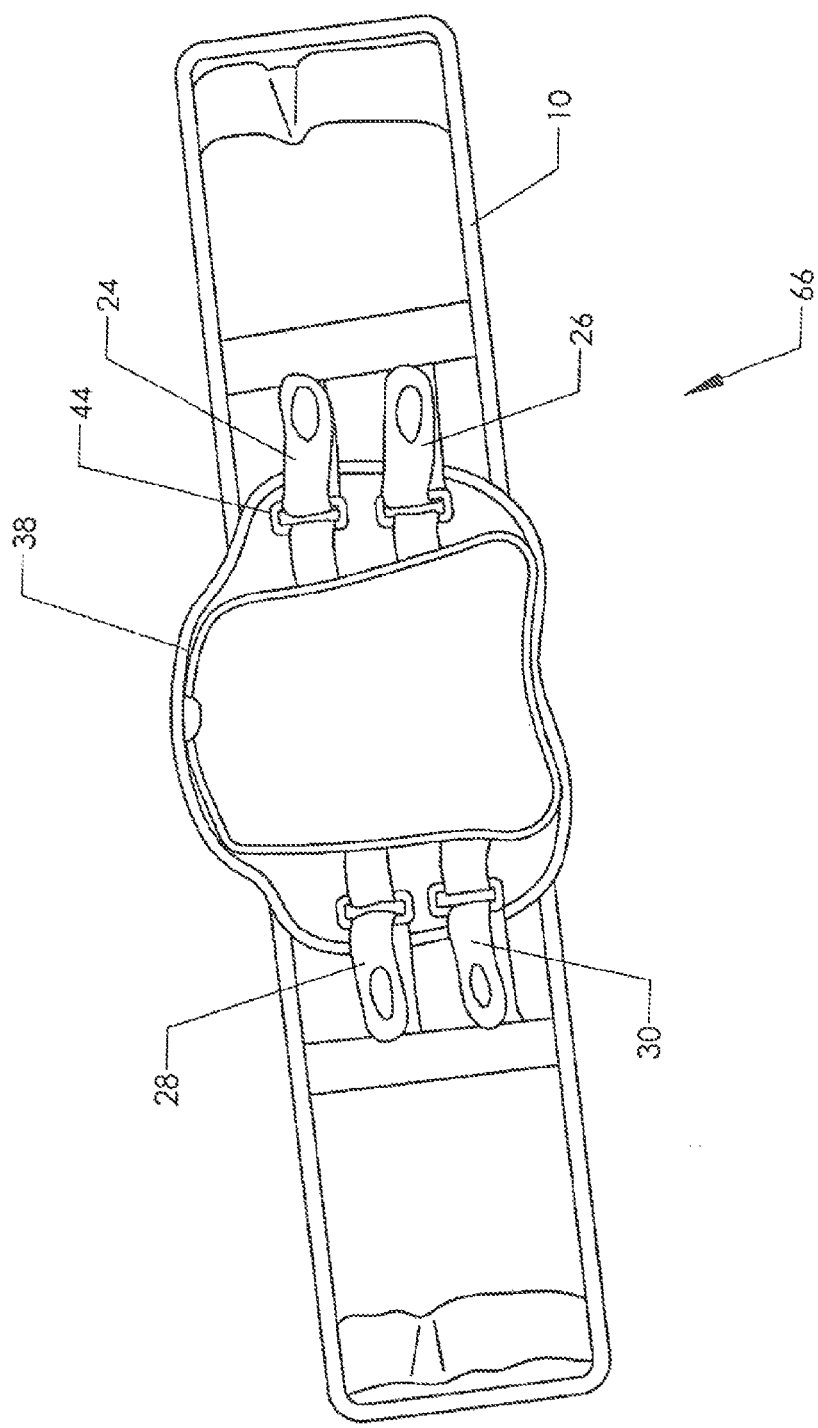
FIG. 6 is a perspective view, showing the cover panel and belt assembled together.

FIG. 6 shows cover panel 38 in place on belt 10 to form assembly 66. The cover panel 38 is held in position using the tension straps 24,26,28,30. The tension straps 24,26,28,30 attached to belt 10 are threaded through the corresponding strap loops 44,46,48,50 on cover panel 38. As an example, tension strap 24 is threaded through strap loop 44 and pressed back on itself. The assembly 66 is thus united so that it may be handled as one unit and placed on the user as one unit. In addition, the inclusion of the tension straps 24,26,28,30 allow the assembly 66 to be progressively tightened after it is in place as will be explained in detail later.

Figure 7:
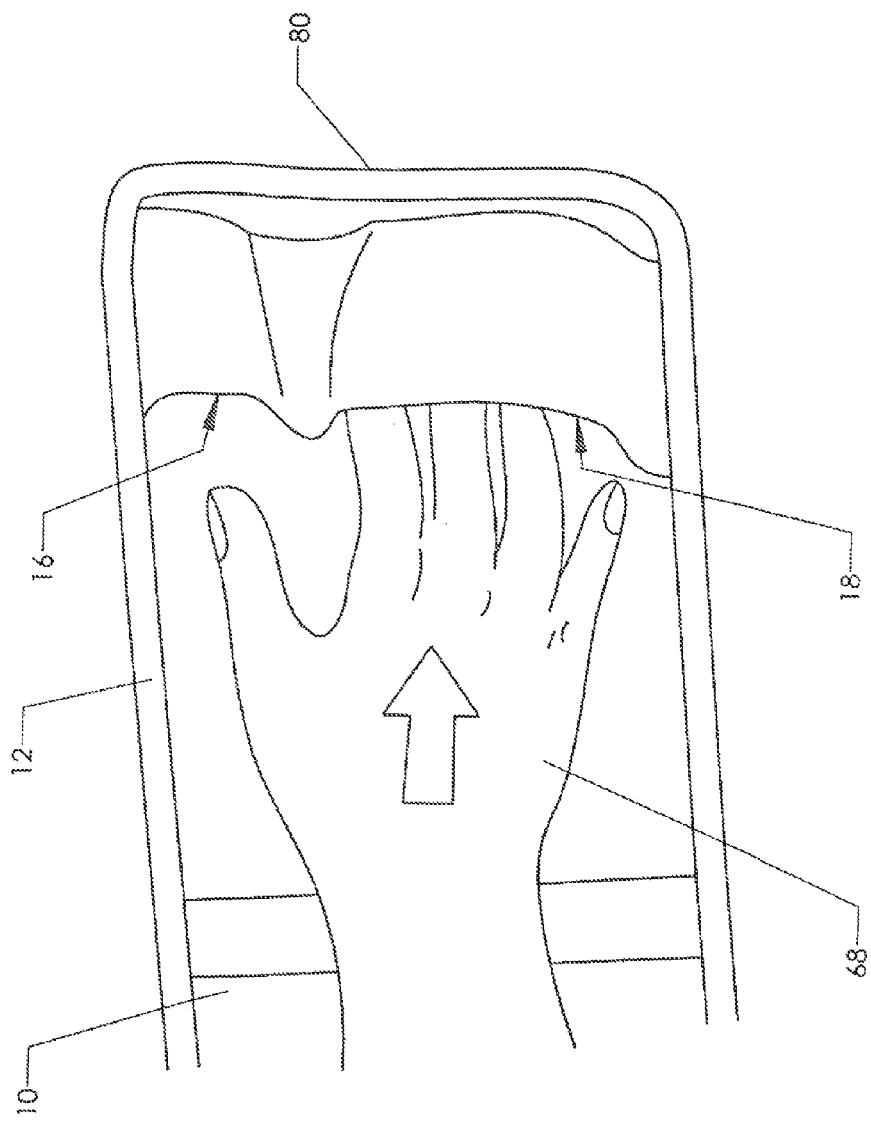
FIG. 7 is a detailed perspective view, showing how the inclusion of finger and thumb pockets on the belt aids the patient in installing the belt.

The reader will recall from the prior description that each side of belt 10 preferably includes a pocket to facilitate placement of belt 10. FIG. 7 shows an embodiment of the right pocket in detail. In the embodiment shown in FIG. 7, the right pocket is divided into two portions—right thumb pocket 16 and right finger pocket 18. Right hand 72 is inserted into the two pockets as shown.

Figure 8:
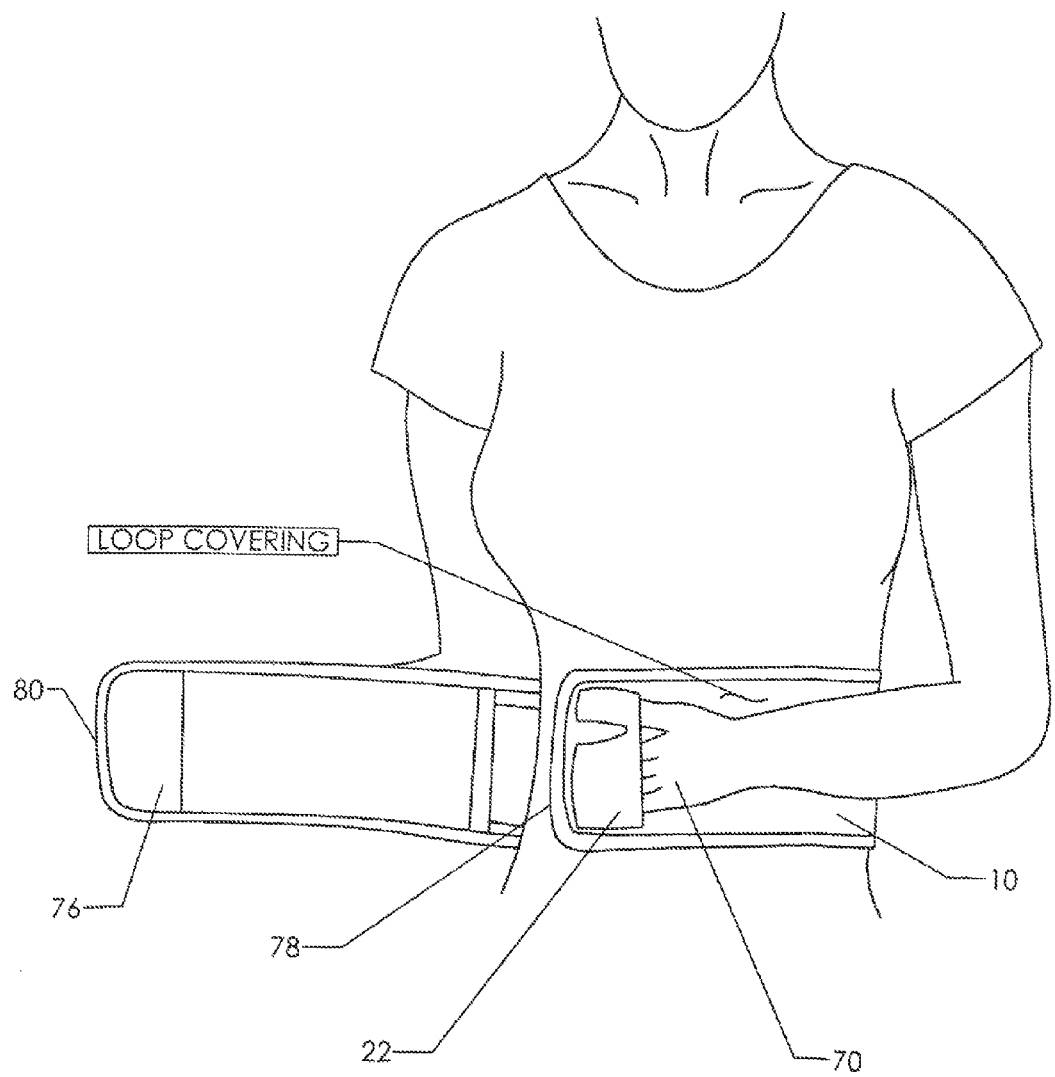
FIG. 8 is a perspective view, showing a patient applying the belt.
Figure 9:
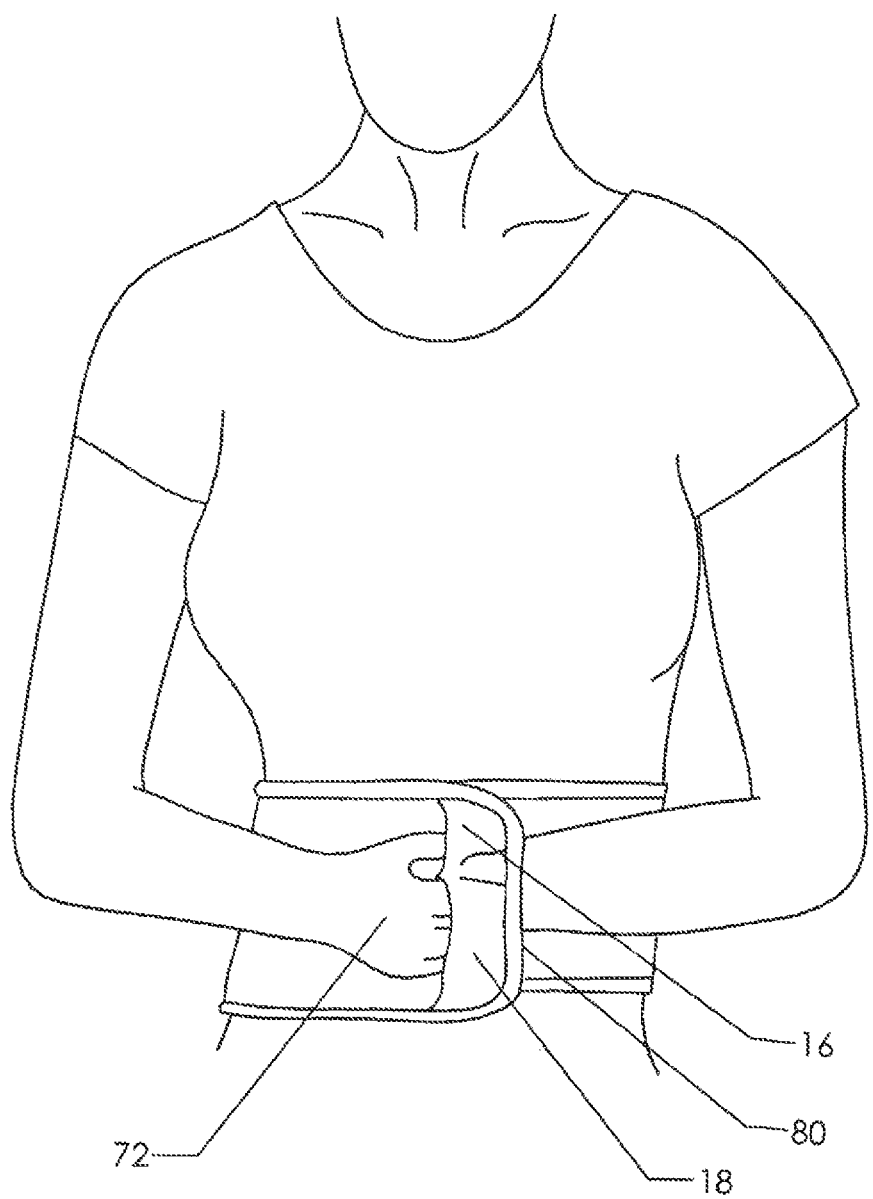
FIG. 9 is a perspective view, showing a patient applying the belt.

As further shown in FIGS. 8 and 9, the pockets facilitate proper placement of belt 10. In FIG. 8, left hand 70 is inserted into left thumb pocket 20 and left finger pocket 22 proximate left edge 78. Right hand 72 is placed in the corresponding right thumb pocket 16 and right finger pocket 18 (not seen by the viewer) proximate right edge 80. Left hand 70 is placed over the abdomen—holding the left portion of belt 10 as shown in FIG. 8. Right hand 72 is extended away from the body to hold right edge 80 clear.

As shown in FIG. 9, right hand 72 is then placed over left hand 70. Hook panel 76 will be pressed against the loop covering on the outward facing side of belt 10. The left hand 70 and right hand 72 are removed from the pockets. Belt 10 will remain in position. The reader will recognize that in the embodiment shown in FIG. 9, right edge 80 overlaps left edge 78 (not seen by the viewer). This overlap may be varied in order to adjust the circumference of belt 10 to suit the needs of the user's anatomy. The belt is essentially a loop of material with a break in it. The break is closed by overlapping the two ends.

Figure 10:
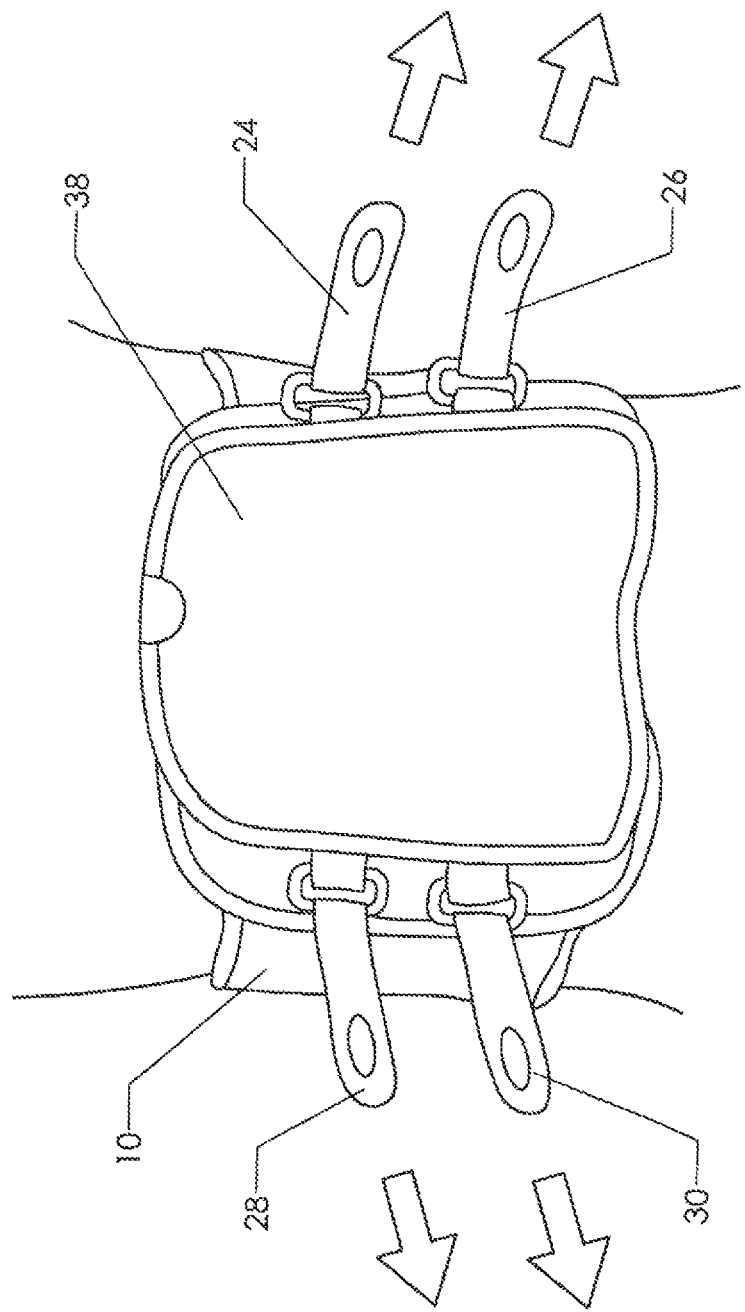
FIG. 10 is a perspective view, showing the cover panel being applied to the belt.
Figure 11:
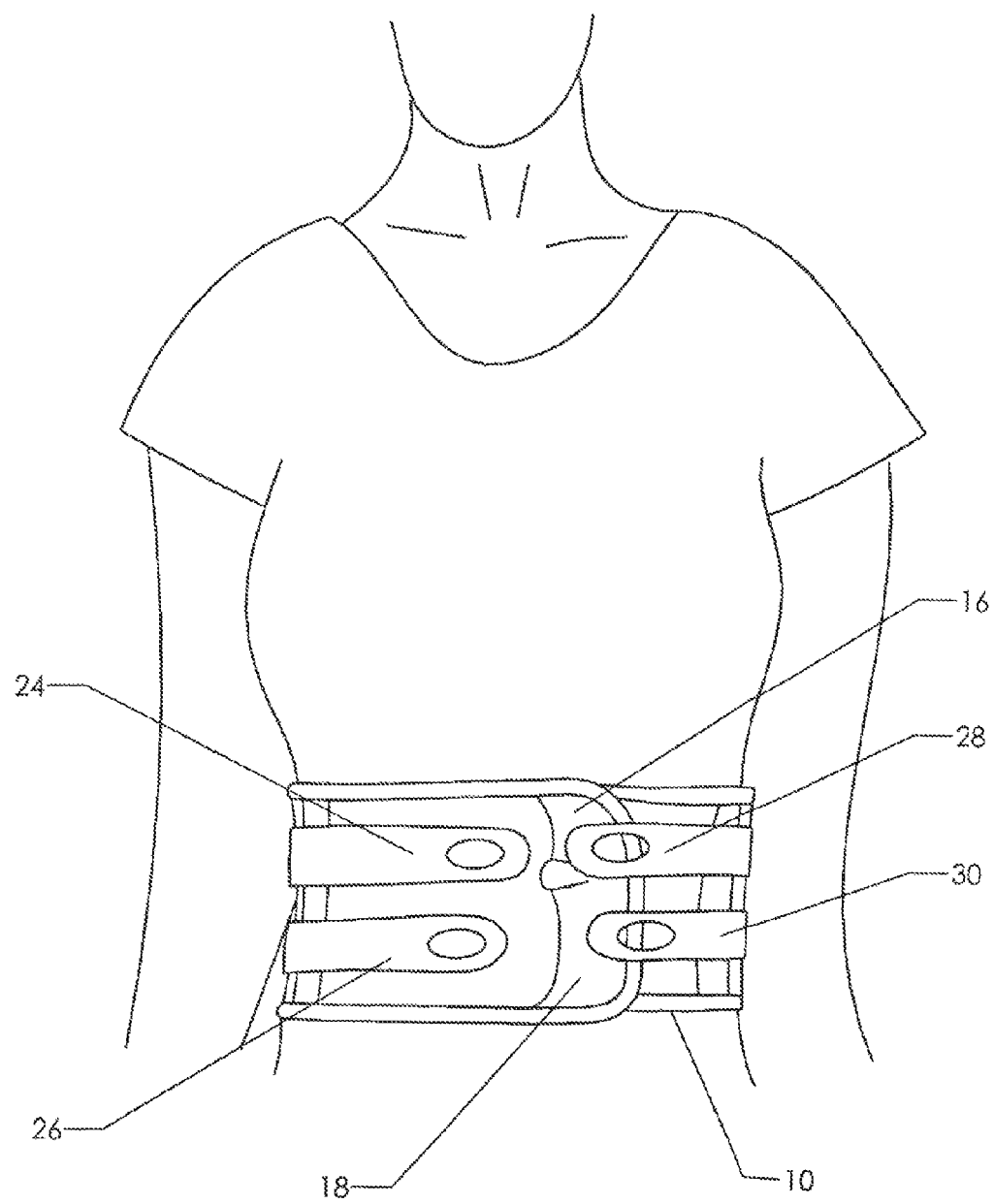
FIG. 11 is a perspective view, showing the belt secured in position on a patient.

When cover panel 38 is attached to belt 10, and assembly 66 is fastened onto the user as shown in FIG. 9, the assembly 66 may be also tightened to create a more desired fit. FIGS. 10 and 11 show this process.

FIG. 10 shows the tightening of tension straps 24,26,28,30 from the vantage point behind the user of belt 10. With the belt 10 positioned around the user's abdomen, the tension straps 24,26,28,30 may be grasped and progressively tightened. In the embodiment shown in FIG. 10, a gripping feature such as an oval hole provided through the end of each tension strap 24,26,28,30 is included so that the user may easily grasp the tension straps 24,26,28,30 and pull.

FIG. 11 shows an example of the completed tightening process. In the embodiment shown FIG 11, the free end of each of the tension straps 24,26,28,30 is secured to belt 10.

Figure 12:
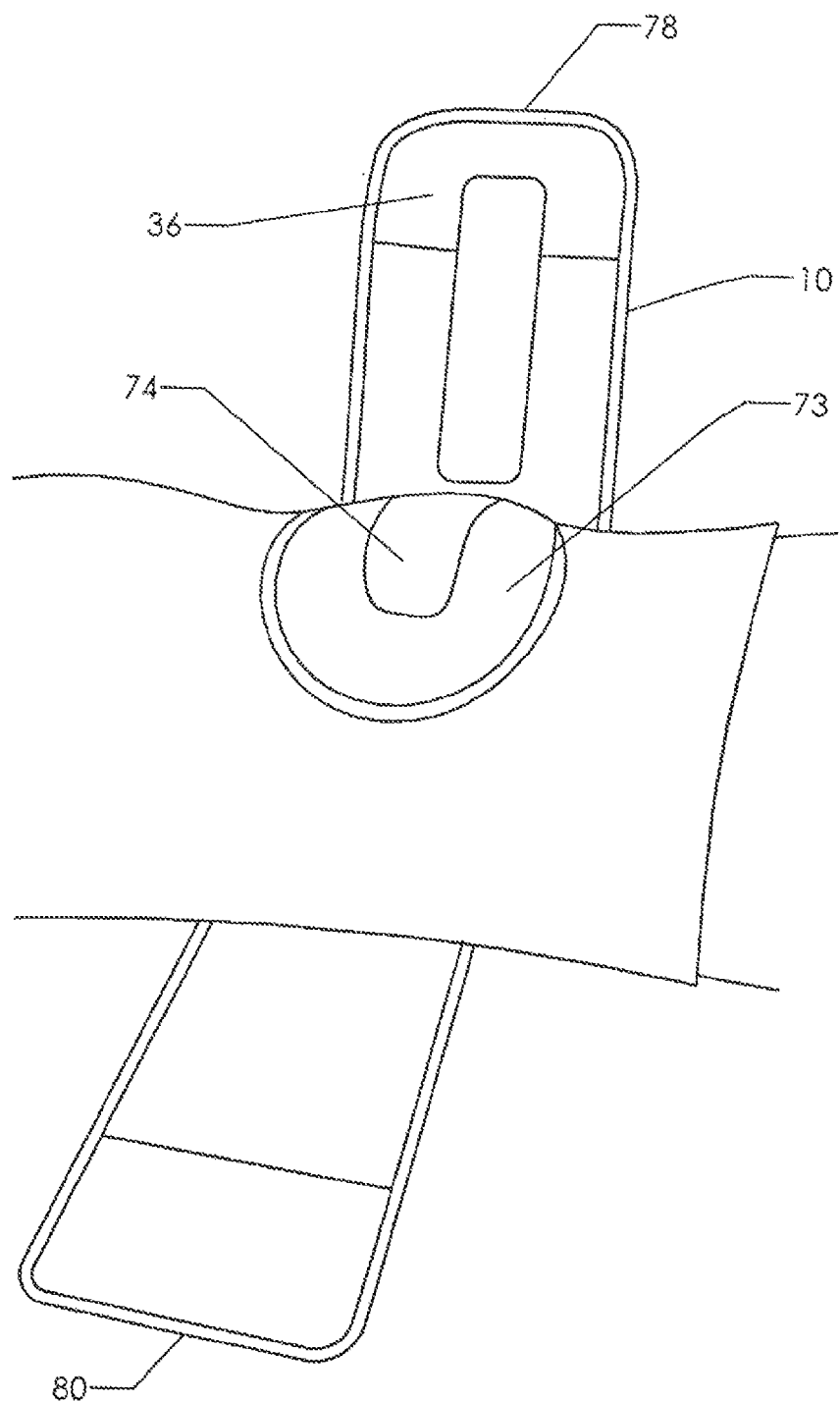
FIG. 12 is a perspective view, showing the belt being applied with an abdominal pad.

Other components may be added to belt 10. For example, FIG. 12 shows an abdominal pad 73 placed on the user's abdomen. Abdominal pad 73 is used to spread the force of belt 10 across the patient's abdomen. Abdominal pad 73 is preferably provided in a variety of sizes and possibly shapes.

On the outward facing side (i.e. the side facing away from the user) of abdominal pad 73 is a hook panel 74. The hook panel 74 generally is located in the center of abdominal pad 73. Hook panel 74 preferably is made of any material that is similarly found in a VELCRO® hook fastener. In cooperation with hook panel 74, a loop panel 34 is provided on belt 10 proximate left edge 78. The exposed area of loop panel 34 preferably is covered in loop covering. The loop covering can be made of any material that is similarly found in a VELCRO® loop fastener. Loop panel 34 is positioned to engage hook panel 74 when belt 10 is installed in the previously-described way (i.e. overlapping right edge 80 over left edge 78). Abdominal pad 73 is thereby properly positioned with respect to belt 10. Even if belt 10 is removed and reinstalled, hook panel 74 will remain engaged to loop panel 34 and retain the proper position.

Figure 13:
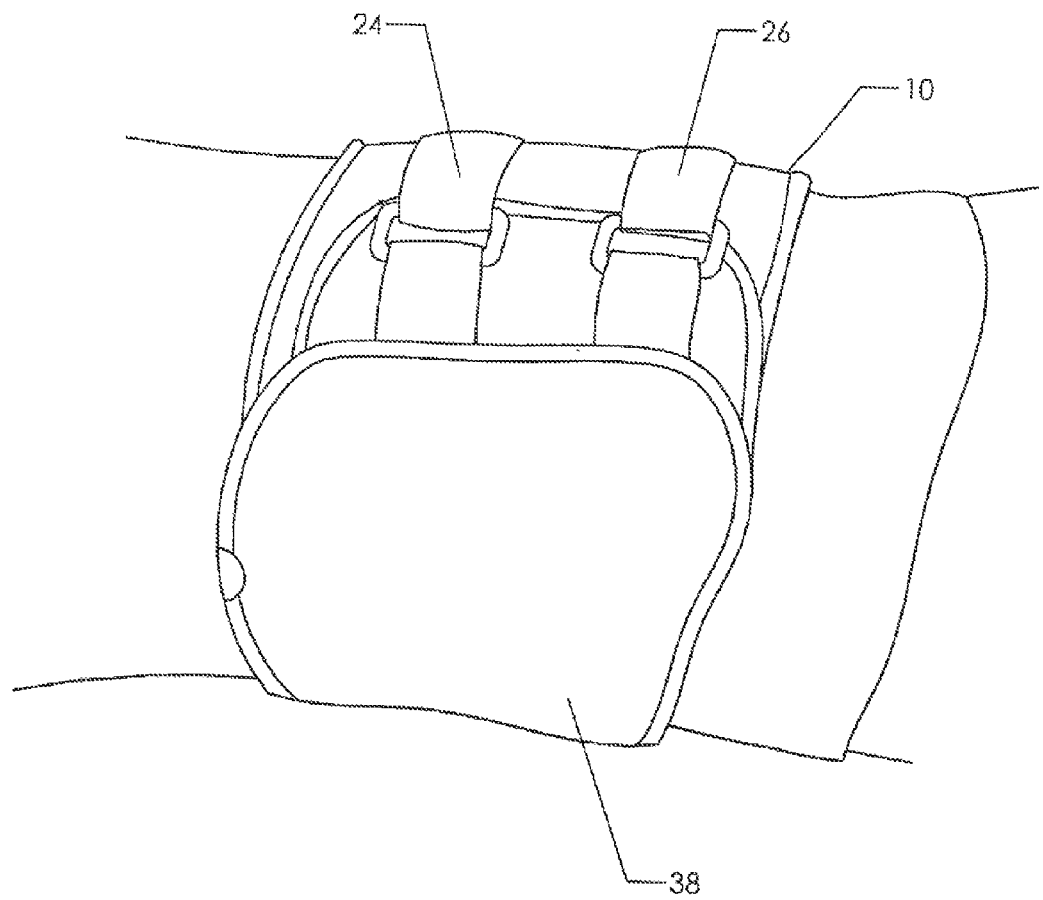
FIG. 13 is a perspective view, showing a patient placed in a position where the cover panel may be opened with the belt still in place.
Figure 14:
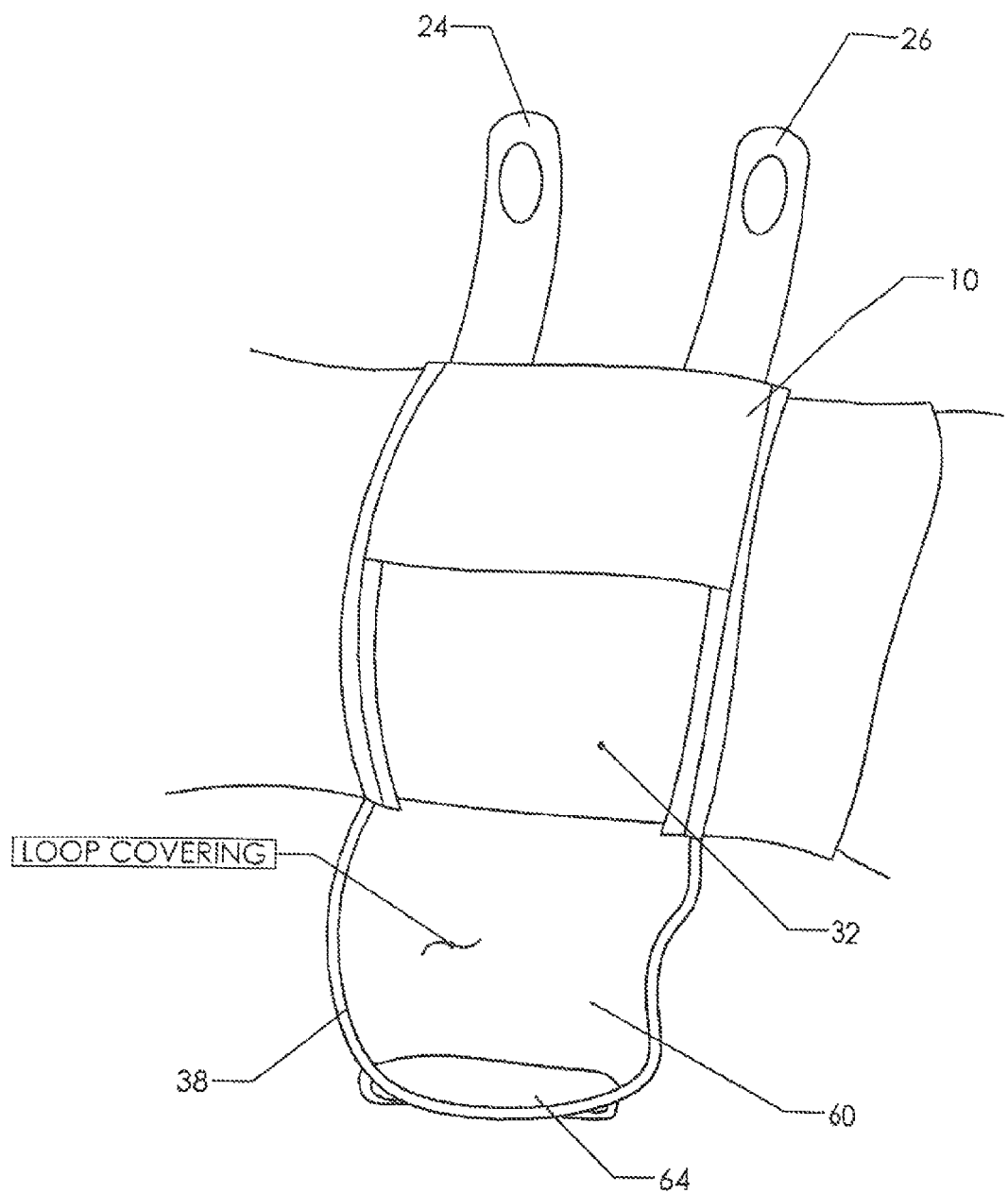
FIG. 14 is a perspective view, showing the cover panel opened to reveal the window in the belt.

One of the advantages of the present invention is that it allows cryo therapy cold packs to be added or exchanged without requiring the removal of belt 10. FIGS. 13-16 illustrate an example of this process. FIG. 13 shows belt 10 and cover panel 38 is placed on the user. Having access to cover panel 38, tension straps 24 and 26 can be disconnected from belt 10 and the right hook panel 64 is freed from the loop covering on belt 10. The right side of cover panel 38 now is free to swing open. FIG. 14 shows the right side of the cover panel 38 open revealing inward facing surface 60.

Figure 15:
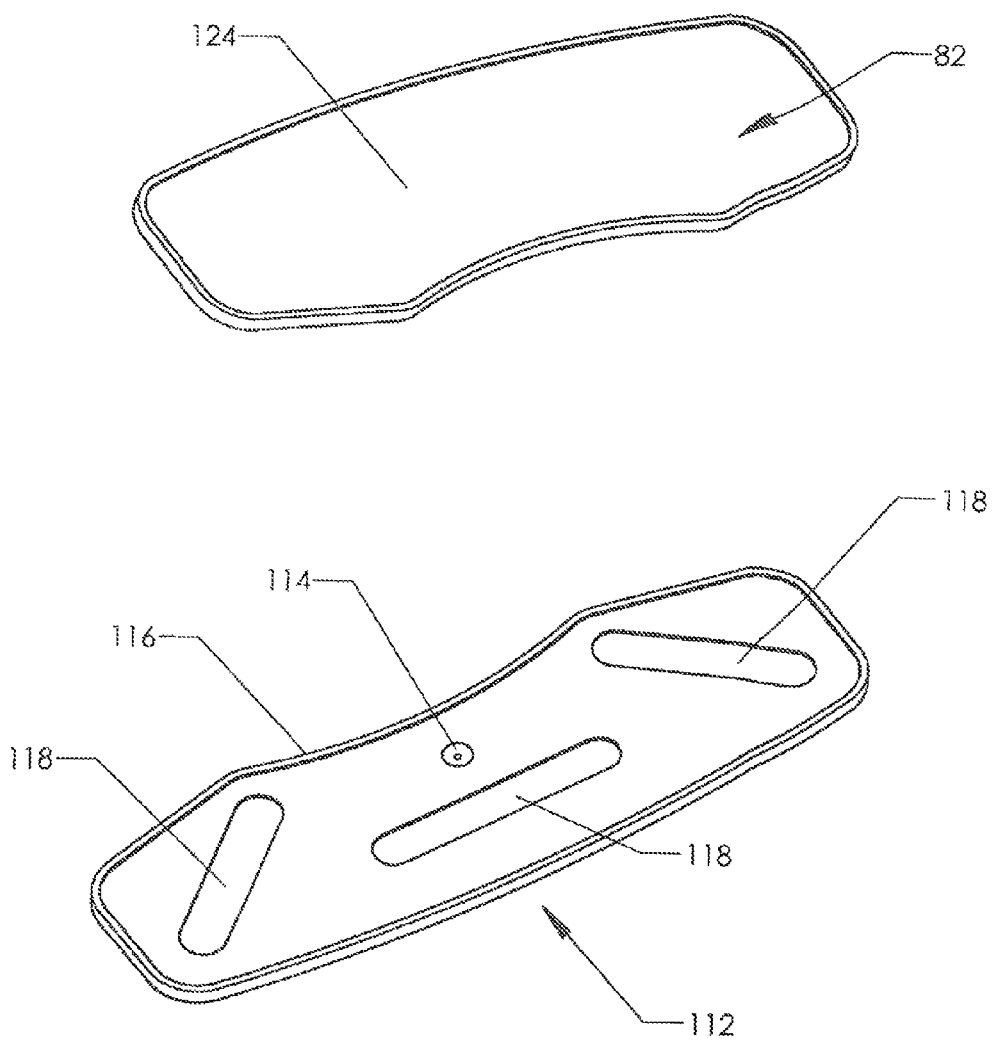
FIG. 15 is a perspective view, showing a pair of cold packs.

FIG. 15 shows two cold packs 112 which are suitable for application to the lumbar area. The two cold packs 12 are identical. Each cold pack 112 has two sides. Soft surface 82 is a smooth surface which may be placed directly against skin. This surface is facing upward for cold pack 112 illustrated near the top of FIG. 15.

The opposite surface is intended to face away from the skin. This opposite surface is facing upward for cold pack 112 illustrated near the bottom of FIG. 15. Cold pack 112 can include one or more hook panels 118. Hook panels 118 preferably are made of any material that is similarly found in a VELCRO® hook fastener. In the embodiment shown in FIG. 15, cold pack 112 includes the optional features, relief 116 and vent 114. Relief 116 allows cold pack 112 to better conform to portions of a person's anatomy. Vent 114 allows the volume inside cold pack 112 to freely expand and air to escape when necessary.

Figure 16:
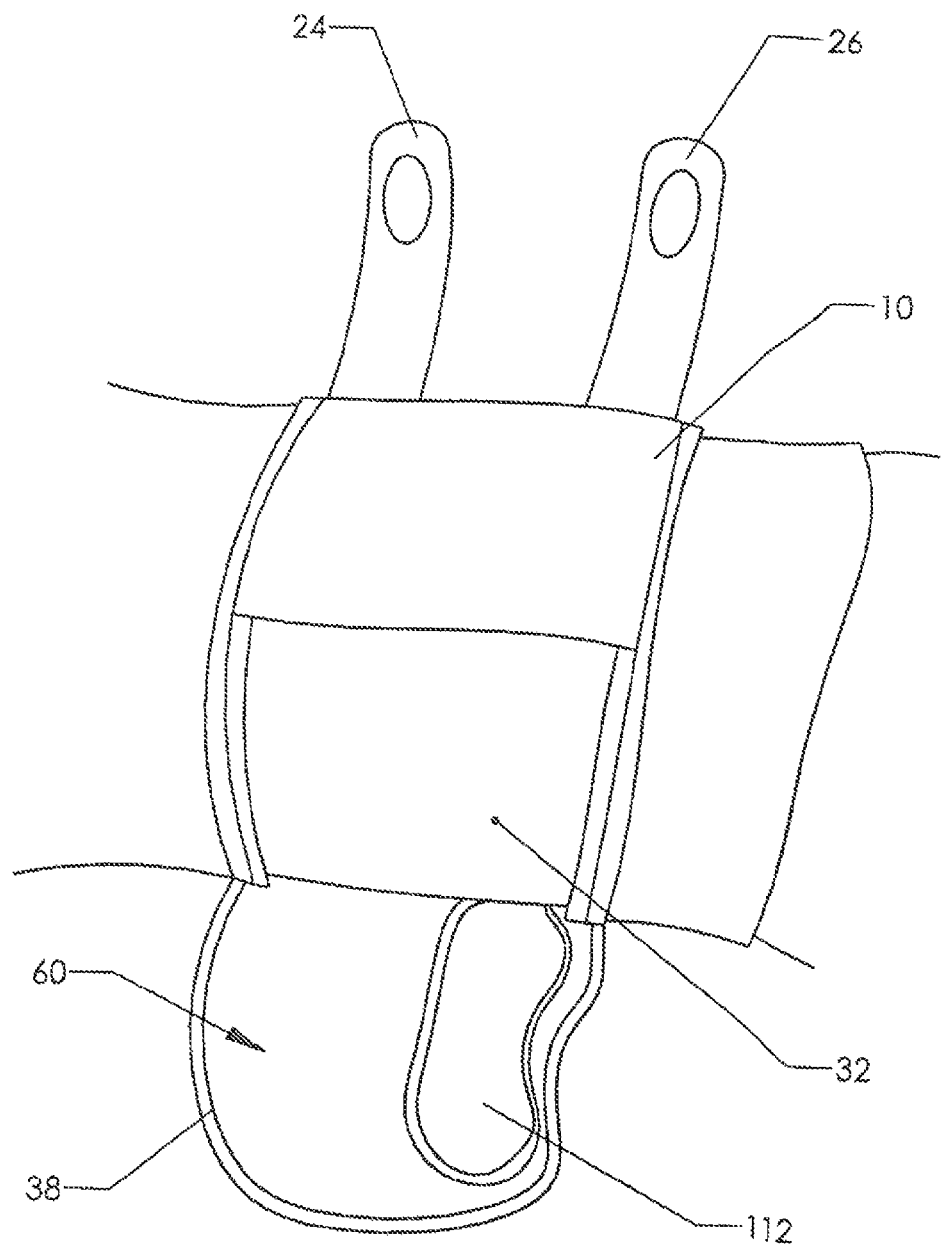
FIG. 16 is a perspective view, showing a cold pack of FIG. 15 being applied to the cover panel.

FIG. 16 shows a cold pack 112 attached to cover panel 38. The cold pack 112 is placed on inward facing surface 60 of cover panel 38. Hook panels 118 on cold pack 112 attaches to the loop covering on inward facing surface 60 of cover panel 38. Cold pack 112 may be placed in a variety and many different positions. As previously mentioned, more than one cold pack 112 may be placed on the inward surface 60 of cover panel 38.

Once cold pack 112 is in the desired position, cover panel 38 is closed covering window 32. Right hook panel 64 will engage the loop covering on belt 10 and hold cover panel 38 in place. Tension straps 24 and 26 may be reattached and tightened to complete the process.

Those skilled in the art will recognize that the process thus described allow for the quick exchange of cold packs. During cryo therapy to the lumbar region, it is necessary to exchange cold packs approximately every four hours. Using the present invention, the exchange may be made without removing the belt. One simply opens a panel providing access to the existing cold packs; the existing cold packs are peeled away and replaced with new cold packs. The panel then is closed.

Those skilled in the art will also recognize that the convenient access to the lumbar region allows a wound dressing to be more rapidly inspected and changed. Further, the present invention facilitates the addition of other treatment devices, such as a TENS unit.

In any instance, the belt remains around the person's anatomy. The belt's presence provides structural reinforcement, which is particular important in cases where the lumbar fascia has been incised. It is important to limit motion in such cases. The cover panel not only retains the cold packs, it also provides a significant retention force across a person's lumbar area.

The preceding description contains significant detail regarding the novel aspects of the present invention. It should not be construed, however, as limiting the scope of the invention but as providing illustrations of the preferred embodiments of the invention. Many more embodiments following the same principles will occur to those skilled in the art. As a first example, the order of the process presented in the descriptions of how the belt is applied and removed are generally unimportant. One may choose to attach the cover panel prior to applying the belt. One may also choose to attach the cover panel after the belt is in place. As a second example, snaps or buckles could be substituted for the hook-and-loop attachments described. As a third example, one side of the cover panel could be permanently attached to the belt, leaving the other side to swing open. Accordingly, the scope of the invention should be fixed by the following claims rather than by the examples given.

The invention claimed is:

1. A method for applying an encircling belt to a patient's waist, comprising:
   a. providing a belt having a top edge, a bottom edge, a right edge, a left edge, an outward facing side, and an inward lacing side;
   b. providing a right pocket proximate said right edge, said right pocket having
      i. an opening accessible from said outward facing side,
      ii. said opening facing away from said right edge,
      iii. a closed end opposite said opening;
   c. providing a left pocket proximate said left edge, said left pocket having
      i. an opening accessible from said outward facing side,
      ii. said opening facing away from said left edge,
      iii. a closed end opposite said opening;
   d. providing a loop covering on a substantial portion of said outward facing side of said belt;
   e. providing a hook panel on said inward facing side of said belt proximate said right edge;
   f. placing a right hand of said patient in said right pocket;
   g. placing a left hand of said patient in said left pocket;
   h. wrapping said belt around said patient's waist;
   i. placing said left hand proximate said patient's waist while said left hand remains in said left pocket;
   j. placing said right hand over said left hand while said left hand remains in said left pocket and said right hand remains in said right pocket; and k. pressing said right hand in toward said waist so that said hook panel on said inward facing side of said belt presses against said loop covering on said outward facing side of said belt, thereby securing said belt to itself.

2. A method for applying an encircling belt to a patient's waist as recited in claim 1, further comprising after said belt is secured to itself, withdrawing said right and left hands from said right and left pockets.

3. A method for applying an encircling belt to a patient's waist as recited in claim 1, wherein:
   a. said right pocket is divided into a right thumb pocket and a right finger pocket;
   b. said closed end of said right pocket is formed by a web separating said right thumb pocket front said right finger pocket;
   c. said left pocket is divided into a left thumb pocket and a left finger pocket; and
   d. said closed end of said left pocket is formed by a web separating said left thumb pocket from said left finger pocket.

4. A method for applying an encircling belt to a patient's waist as recited in claim 1, further comprising:
   a. providing a loop covering on a portion of said inward facing side of said belt;
   b. providing a cold pack containing a cooling medium;
   c. said cold pack including a hook panel; and
   d. applying said cold pack to said inward facing side of said belt by pressing said hook panel of said cold pack against said loop covering on said inward facing side of said belt.

5. A method for applying an encircling belt to a patient's waist as recited in claim 1, further comprising:
   a. providing a window in said belt;
   b. providing a cover panel, with said cover panel being sized to cover said window;
   c. said cover panel including an inward facing surface, with said inward facing surface being covered in loop material;
   d. providing a cold pack containing a cooling medium;
   e. said cold pack including a hook panel;
   f. applying said belt to said patient with said window being positioned over said patient's lumbar region;
   g. attaching said cover panel to said belt so that said cover panel lies over said window;
   h. uncovering said window by detaching at least a portion of said cover panel from said belt, thereby revealing said inward facing surface of said cover panel;
   i. attaching said cold pack to said inward facing surface of said cover panel by pressing said hook panel of said cold pack against said loop material on said inward facing surface; and
   j. recovering said window by reattaching said at least a portion of said cover panel to said belt, thereby placing said cold pack in contact with said patient's lumbar region.

6. A method for applying an encircling belt to a patient's waist as recited in claim 5, wherein:
   a. said cover panel includes a right hook panel and a left hook panel; and
   b. said cover panel is attached to said belt by pressing said right and left hook panels on said cover panel against said loop panel on said belt.

7. A method for applying an encircling belt to a patient's waist as recited in claim 5, wherein said cover panel is attached to said belt by a plurality of adjustable tension straps.

8. A method for applying an encircling belt to a patient's waist, comprising:
   a. providing an elongated belt with a right edge, a left edge, an outward facing side, and an inward facing side;
   b. providing a right pocket proximate said right edge, said right pocket having an opening distal to said right edge and a closed end proximate to said right edge, with said opening being accessible from said outward facing side of said belt;
   c. providing a left pocket proximate said left edge, said left pocket having an opening distal to said left edge and a closed end proximate said left edge, with said opening being accessible from said outward facing side of said belt;
   d. providing a loop covering on a substantial portion of said outward facing side of said belt;
   e. providing a hook panel on said inward facing side of said belt proximate said right edge;
   f. placing a right hand of said patient in said right pocket;
   g. placing a left hand of said patient in said left pocket;
   h. wrapping said belt around said patient's waist;
   i. placing said left hand proximate said patient's waist while said left hand remains in said left pocket;
   j. placing said right hand over said left hand while said left hand remains in said left pocket and said right hand remains in said right pocket; and
   k. pressing said right hand in toward said waist so that said hook panel on said inward facing side of said belt presses against said loop covering on said outward facing side of said belt, thereby securing said belt to itself.

9. A method for applying an encircling belt to a patient's waist as recited in claim 8, further comprising after said belt is secured to itself, withdrawing said right and left hands from said right and left pockets.

10. A method for applying an encircling belt to a patient's waist as recited in claim 8, wherein:
    a. said right pocket is divided into a right thumb pocket and a right finger pocket;
    b. said closed end of said right pocket is formed by a web separating said right thumb pocket from said right finger pocket;
    c. said left pocket is divided into a left thumb pocket and a left finger pocket; and
    d. said closed end of said left pocket is formed by a web separating said left thumb pocket from said left finger pocket.

11. A method for applying an encircling belt to a patient's waist as recited in claim 8, further comprising:
    a. providing a loop covering on a portion of said inward facing side of said belt;
    b. providing a cold pack containing a cooling medium;
    c. said cold pack including a hook panel; and
    d. applying said cold pack to said inward facing side of said belt by pressing said hook panel of said cold pack against said loop covering on said inward facing side of said belt.

12. A method for applying an encircling belt to a patient's waist as recited in claim 8, further comprising:
    a. providing a window in said belt;
    b. providing a cover panel, with said cover panel being sized to cover said window;
    c. said cover panel including an inward facing surface, with said inward facing surface being covered in loop material;
    d. providing a cold pack containing a cooling medium;
    e. said cold pack including a hook panel;
    f. applying said belt to said patient with said window being positioned over said patient's lumbar region;

g. attaching said cover panel to said belt so that said cover panel lies over said window;
h. uncovering said window by detaching at least a portion of said cover panel from said belt, thereby revealing said inward facing surface of said cover panel;
i. attaching said cold pack to said inward facing surface of said cover panel by pressing said hook panel of said cold pack against said loop material on said inward facing surface; and
j. recovering said window by reattaching said at least a portion of said cover panel to said belt, thereby placing said cold pack in contact with said patient's lumbar region.

13. A method for applying an encircling belt to a patient's waist as recited in claim 12, wherein:
   a. said cover panel includes a right hook panel and a left hook panel; and
   b. said cover panel is attached to said belt by pressing said right and left hook panels on said cover panel against said loop panel on said belt.

14. A method for applying an encircling belt to a patient's waist as recited in claim 12, wherein said cover panel is attached to said belt by a plurality of adjustable tension straps.

15. A method for applying an encircling belt to a patient's waist, comprising:
   a. providing an elongated belt having an outward facing side and an inward facing side;
   b. looping said belt around said patient's waist, said loop including a break, with said break being bounded by a right edge and a left edge;
   c. providing a right pocket proximate said right edge, said right pocket having an opening distal to said right edge and a closed end proximate to said right edge, with said opening being accessible from said outward facing side of said belt;
   d. providing a left pocket proximate said left edge, said left pocket having an opening distal to said left edge and a closed end proximate said left edge, with said opening being accessible from said outward facing side of said belt;
   e. providing a loop covering on a substantial portion of said outward facing side of said belt;
   f. providing a hook panel on said inward facing side of said belt proximate said left edge;
   f. placing a right hand of said patient in said right pocket;
   g. placing a left hand of said patient in said left pocket;
   h. placing said right hand proximate said patient's waist while said right hand remains in said right pocket;
   i. placing said right hand over said left hand while said left hand remains in said left pocket and said right hand remains in said right pocket; and
   k. pressing said left hand in toward said waist so that said hook panel on said inward facing side of said belt presses against said loop covering on said outward facing side of said belt, thereby securing said belt to itself.

16. A method for applying an encircling belt to a patient's waist as recited in claim 15, further comprising after said belt is secured to itself, withdrawing said right and left hands from said right and left pockets.

17. A method for applying an encircling belt to a patient's waist as recited in claim 15, wherein:
   a. said right pocket is divided into a right thumb pocket and a right finger pocket;
   b. said closed end of said right pocket is formed by a web separating said right thumb pocket from said right finger pocket;
   c. said left pocket is divided into a left thumb pocket and a left finger pocket; and
   d. said closed end of said left pocket is formed by a web separating said left thumb pocket from said left finger pocket.

18. A method for applying an encircling belt to a patient's waist as recited in claim 15, further comprising:
   a. providing a loop covering on a portion of said inward facing side of said belt;
   b. providing a cold pack containing a cooling medium;
   c. said cold pack including a hook panel; and
   d. applying said cold pack to said inward facing side of said belt by pressing said hook panel of said cold pack against said loop covering on said inward facing side of said belt.

19. A method for applying an encircling belt to a patient's waist as recited in claim 15, further comprising:
   a. providing a window in said belt;
   b. providing a cover panel, with said cover panel being sized to cover said window;
   c. said cover panel including an inward facing surface, with said inward facing surface being covered in loop material;
   d. providing a cold pack containing a cooling medium;
   e. said cold pack including a hook panel;
   f. applying said belt to said patient with said window being positioned over said patient's lumbar region;
   g. attaching said cover panel to said belt so that said cover panel lies over said window;
   h. uncovering said window by detaching at least a portion of said cover panel from said belt, thereby revealing said inward facing surface of said cover panel;
   i. attaching said cold pack to said inward facing surface of said cover panel by pressing said hook panel of said cold pack against said loop material on said inward facing surface; and
   j. recovering said window by reattaching said at least a portion of said cover panel to said belt, thereby placing said cold pack in contact with said patient's lumbar region.

20. A method for applying an encircling belt to a patient's waist as recited in claim 19, wherein:
   a. said cover panel includes a right hook panel and a left hook panel; and
   b. said cover panel is attached to said belt by pressing said right and left hook panels on said cover panel against said loop panel on said belt.

* * * * *